United States Patent

O'Connell et al.

Patent Number: 5,125,265
Date of Patent: Jun. 30, 1992

[54] CONTAMINATION CAPACITANCE PROBE SYSTEM

[75] Inventors: Thomas A. O'Connell, North Kingston; Thomas A. Frank, Newport, both of R.I.

[73] Assignee: The United States of America as represented by the Secretary of the Navy, Washington, D.C.

[21] Appl. No.: 594,537

[22] Filed: Oct. 9, 1990

[51] Int. Cl.$^5$ ............................................. G08B 21/00
[52] U.S. Cl. ................................. 73/61.41; 324/664; 324/667
[58] Field of Search ............... 324/661, 663, 664, 665, 324/667, 658; 73/61 R, 61.1 R

[56] References Cited

U.S. PATENT DOCUMENTS

| | | | |
|---|---|---|---|
| 1,960,168 | 5/1934 | Schoenberg | 73/664 |
| 3,816,811 | 6/1974 | Cmelik | 324/667 |
| 4,114,090 | 9/1978 | Poskitt | 324/667 |
| 4,638,305 | 1/1987 | Sutton | 324/664 |
| 4,683,904 | 8/1987 | Iltis | 324/667 |
| 4,710,757 | 12/1987 | Haase | 324/664 |
| 4,751,842 | 6/1988 | Ekrann et al. | 73/61.1 R |
| 4,916,940 | 4/1990 | Mougne | 324/664 |

Primary Examiner—Hezron E. Williams
Assistant Examiner—Craig Miller
Attorney, Agent, or Firm—Michael J. McGowan; Prithvi C. Lall; Michael F. Oglo

[57] ABSTRACT

A contamination capacitance probe system is disclosed that capacitively monitors whether or not two or more fluids or materials that have to remain separated have been mixed or mingled and that provides first and second control signals respectively representative of the unmingled and mingled conditions. The system includes a capacitance sensor constituted by spaced-apart first and second capacitor plates of preselected size and spacing. The plate size and spacing is selected to render negligible any effect that the different materials or fluids or materials might have on the capacitance of the sensor. Circuit means are disclosed that includes a capacitance to frequency convertor, a frequency to voltage convertor, and a Schmidt trigger operative to provide the first and second control signals. The contamination capacitance probe system of the present invention is operable with any two or more fluids or materials having different dielectric constants and that are either immiscible or miscible.

4 Claims, 1 Drawing Sheet

CONTAMINATION CAPACITANCE PROBE SYSTEM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

This invention is directed to the field of measurement and testing, and more particularly, to a contamination capacitance probe system.

(2) Description of the Prior Art

In many applications different systems and subsystems employ or are exposed to two or more fluids or materials where their mutual separation is essential to achieving the intended control or other action, and where their co-mingling effects an undesirable contamination. Examples are water or other contaminate in the fuel of a fuel burning system; metal, water or other contaminate in the motor oil of an internal combustion engine, and seawater in an hydraulic ballast and buoyancy compensation unit of an unmanned undersea vehicle, among others.

Whenever the fluids or materials that should be kept separated are caused to mingle, due to a failure of some component, system, subsystem or other cause, the ability of the component, system or subsystem or other device to perform its function or intended design mission becomes compromised. In the hydraulic ballast and buoyancy compensation unit of an unmanned undersea vehicle, for example, the failure of a rubber bladder that is controllably expanded and contracted by pumping hydraulic oil thereto to displace different quantities of seawater into and out of the ballast tank of the undersea vehicle could prevent the undersea vehicle from trimming to a positive buoyancy state and therewith prevent its surface recovery.

Resistance-type and capacitance-type sensors are known that measure changes in level of a fluid or material in which they are immersed or with which the are brought into contact. The utility of these heretofore known sensors, however, is limited to sensing level changes of a single fluid or material but are generally incapable of responding to and providing a signal representative of two or more fluids or materials having been mixed or mingled. In the case of seawater and oil, for example, the presence of the oil, that acts to coat such prior art level sensors both of the resistance-type and capacitance-type, effectively prevents their ability to respond to the presence of the seawater and oil after they have been mixed or mingled.

SUMMARY OF THE INVENTION

It is accordingly the principal object of the present invention to provide a contamination capacitance probe system that capacitively monitors whether or not two or more fluids or materials that have to remain separated have been mixed or mingled and that provides first and second control signals respectively representative of the unmingled and mingled conditions. The contamination capacitance probe system of the present invention is operable with any two or more fluids or materials having different dielectric constants that are either immiscible or miscible.

In accord with one feature thereof, a capacitance sensor is disclosed having a preselected plate size and plate spacing selected to render negligible any effect that would otherwise arise from coating or other operational impediment of the capacitance sensor by oil or other fluid or material.

In accord with another feature thereof, circuit means are disclosed that respond to the capacitance sensor's capacitance to provide the control signals that respectively indicate either that the two or more fluids or materials remain separated or have been mixed or mingled. In the preferred embodiment, oil and seawater are the two fluids.

BRIEF DESCRIPTION OF THE DRAWINGS

These and other objects, features, and advantages of the present invention will become apparent as the invention becomes understood by referring to the following detailed description of the preferred embodiments and to the drawings, wherein.

DETAILED DESCRIPTION OF THE PREFERRED EMBODIMENTS

Figure 1:
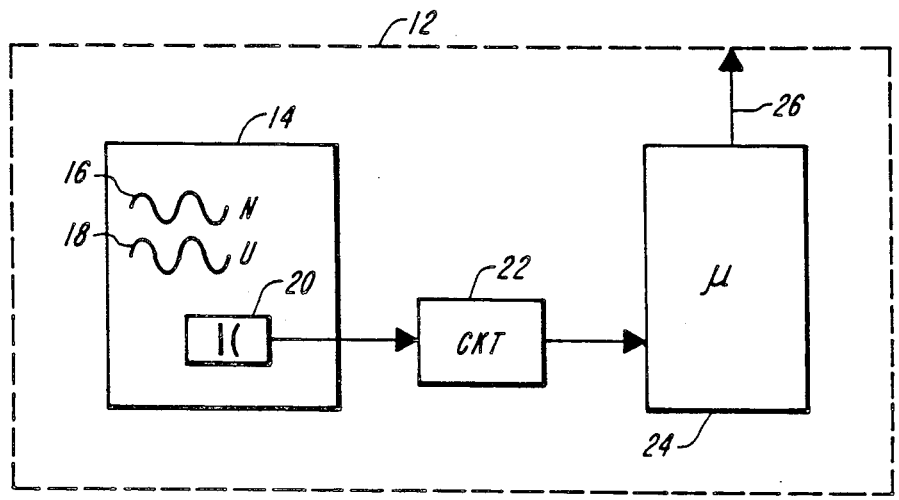
FIG. 1 is a block diagram illustrating the typical environment in which the contamination capacitance probe system of the present invention has utility.

Referring now to FIG. 1, generally illustrated at 10 is a block diagram of a typical applications environment in which the contamination capacitance probe of system the present invention has exemplary utility. A system, subsystem or other device is schematically illustrated in dashed outline 12 that operatively employs two or more fluids or materials to achieve some intended control action or other effect in such manner that the two or more fluids or materials are normally kept separated, but which, due to failure of some system or subsystem or other cause, are undesirably caused to be mixed or mingled, whereby the intended control action or other effect might become compromised, as may be found, for example, in a gas tank subject to water contamination, water or other contamination of motor oil in an internal combustion engine , and seawater contamination of the hydraulic ballast and buoyancy compensation unit of an unmanned undersea vehicle, among others.

Member 14 schematically illustrates the component of device 12 where the mingling or mixing of the two or more fluids or materials exhibits itself, and may be, for the examples given, the gas tank, gas feed line, or hydraulic oil reservoir, respectively of a motor vehicle, internal combustion engine, and hydraulic ballast and buoyancy compensation unit of an undersea vehicle.

Indicia 16, 18, respectively marked "N", "U" for "nominal" and "undesired", schematically represent the two or more fluids or materials that should be kept separated but which, when copresent, are indicative of a possible failure condition. The fluids 16, 18 may be gas and water; oil and water, and oil and seawater, for the examples given.

A capacitive sensor 20 to be described is positioned within the member 14 at a location thereof selected to expose the sensor 20 to the fluid or material, whether the nominal fluid or material 16, the undesired fluid or material 18, or a combination of the two or more fluids or materials 16, 18. A circuit 22 to be described is coupled to the capacitance sensor 20. The circuit 22 responds to the two or more fluids or materials 16, 18 having been mingled or mixed to provide a signal indicative thereof.

A processor 24 or other controller is coupled to the circuit 22 and is responsive to the signal indicative of the two or more fluids or materials having been mixed or mingled to provide a control action, as schematically illustrated by an arrow 26. Such a control action may, for example, be to compensate the device 12 for any effects that may arise from the undesirable mixing or mingling of the two or more fluids or materials 16, 18, or to provide an alarm indicating such mixing or mingling of the fluids, among others.

Figure 2:
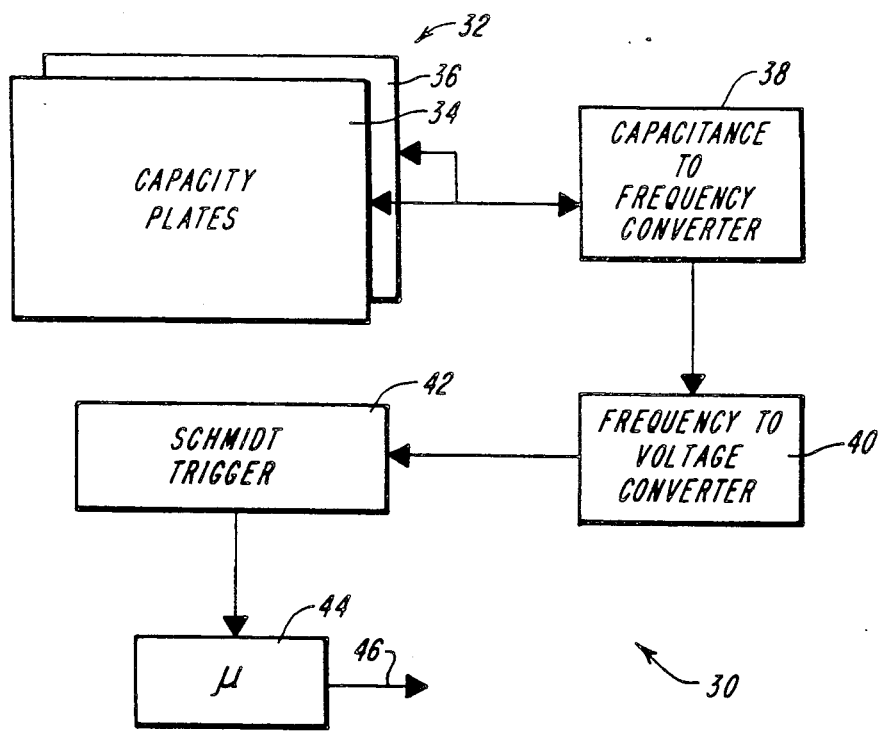
FIG. 2 is a block diagram of the presently preferred embodiment of the novel contamination capacitance probe system of the present invention.

Referring now to FIG. 2, generally designated at 30 is a block diagram illustrating a novel capacitance contamination probe system constructed in accordance with a preferred embodiment of the present invention. The probe system 30 includes a capacitor generally designated at 32 consisting of two metallic plates 34, 36. The plates 34, 36 of the capacitor 32 have a preselected size and spacing selected to render negligible any effect that would otherwise arise from coating or other operational impediment of one, or both, of the plates 34, 36 by the two o more fluids or materials 16, 18 (FIG. 1) having been mingled or mixed. In one preferred embodiment for detecting the presence of seawater and oil, the plates 34, 36 are about ten (10) centimeters by ten (10) centimeters in size and are spaced apart about one and one fourth centimeters (1.25), which has been found to render negligible the effects of oil coating the plates that arises when oil, which is the nominal fluid between the plates, is wholly or partially displaced by seawater, which is the undesired fluid between the plates, as the seawater flows between the plates due to failure of a rubber bladder, not shown, that controls a buoyancy tank, not shown, of an unmanned undersea vessel, not shown. In this embodiment, the plates 32, 34 are disposed at the bottom of an oil reservoir, not shown, of an oil pumping system, not shown, that is connected to the rubber bladder. The rubber bladder displaces different amounts of seawater, depending on the quantity of oil pumped into and out of it, and therewith controls the buoyancy of the buoyancy tank.

A capacitance to frequency converter 38 is connected to the plates 34, 36 of the capacitor 32. The capacitance to frequency converter 38 is responsive to the capacitance between the plates 34, 36 to provide a frequency signal representative thereof. In one presently preferred embodiment, where the capacitor 32 is nominally exposed only to oil, but in the case of a failure condition is undesirably exposed to seawater, which is immiscible in the oil, the capacitance defined between the plates 34, 36 undergoes a shift in value. The dielectric constant of seawater is on the order of thirty-five (35) times greater than that of hydraulic oil.

The capacitance to frequency converter 38 is responsive to change in capacitance and varies its output frequency accordingly. In the presently preferred embodiment, the capacitance to frequency converter 38 is implemented with a "555" capacitance responsive oscillator timing chip commercially available from National Semiconductor, although any other suitable capacitance to frequency converter may be employed as well without departing from the inventive concept. The capacitance to frequency convertor is operative to output a first frequency typically 11,000 Htz., when oil alone is present between the plates 32, 34 of the capacitor 30, and a second predetermined frequency, typically 345 Htz., when seawater is present therebetween due to a failure condition having arisen that mixes the seawater and oil in the hydraulic oil reservoir. As seawater is denser than hydraulic oil, the seawater displaces the oil nominally found between the plates, and therewith changes the dielectric constant of the capacitor 30.

A frequency-to-voltage converter 40 is coupled to the frequency signal output of the capacitance to frequency converter 38. The frequency to voltage converter 40 produces a voltage output signal having an amplitude that is directly proportional to the particular frequency of the variable frequency output signal of the capacitance to frequency converter 48. The frequency to voltage converter 40 preferably is a Model 4702 converter, commercially available from Teledyne Philbrick, although any other suitable frequency to voltage converters may be employed without departing from the inventive concept.

The frequency to voltage converter is operative to output a first predetermined voltage, typically 11.5 volts, when the first predetermined frequency is being output from the capacitance to frequency convertor 38, and a second predetermined voltage, typically 0.1 volts, when the second predetermined frequency is being output therefrom.

A Schmitt trigger 42 is coupled to the frequency to voltage converter 40. The Schmitt trigger 42 threshold is selected to lie between the first and second predetermined voltages output by the frequency to voltage convertor. In response to the voltage signal output by the frequency to voltage convertor 40 exceeding the predetermined threshold, the Schmidt trigger 42 produces an output signal that is representative that the two or more fluids or materials have been undesirably mixed or mingled.

A processor 44 or other control device is coupled to the Schmitt trigger 42. In response to an output signal from the Schmitt trigger 42, the processor 44 provides an output control signal 46. The output control signal 46 may indicate or compensate for the failure that resulted in the two or more fluids or materials having become mixed or mingled.

Many modifications of the presently disclosed invention will become apparent to those skilled in the art without departing from the inventive concept. The contamination capacitance probe system could be used for many applications besides the sensing of seawater in oil of the exemplary application. For example, by varying the dimensions of the capacitor plates, and by tuning both the capacitance responsive oscillator timing chip frequency and the frequency to voltage converter, a wide variety of different contamination types may be sensed. Furthermore, the Schmidt trigger, that provides a good/bad output signal, may be replaced by circuitry that provides a continuously variable or more finely graded output signal, such as would be provided by a bank of comparators or other circuitry. The output control signal could also be used to sound an alarm bell, among other things.

What is claimed is:

1. A contamination capacitance probe system for indicating that at least two fluids having different dielectric constants that should be kept separated have been mingled, comprising:

a capacitor constituted by first and second capacitor plates of preselected dimensions and spaced-apart a preselected dimension that are selected such that the capacitor exhibits a first capacitance whenever the plates thereof are subjected in a first predetermined manner to a nominal one of the two or more fluids having different dielectric constants and exhibits a second capacitance different from the first capacitance whenever the plates thereof are subjected in a second predetermined manner to an undesired at least one of the two or more fluids having different dielectric constants after having been subjected to said nominal one of the two or more fluids and in such a way as to render negligible any residual effect that the nominal fluid had on the plates in their having been first subjected to the nominal fluid, said nominal fluid being oil and said undesired fluid being seawater, said preselected dimensions of said first and second capacitor plates and said preselected dimension by which the first and second capacitor plates are spaced apart being selected to render negligible the effect of residual coating of the first and second plates by the oil upon their being subjected to the seawater, said plates being about ten (10) centimeters by ten (10) centimeters in size and being spaced apart about one and one forth centimeters (1.25); and means coupled to said capacitor and responsive to said first capacitance to provide a signal indication that the first and second plates are being subjected to the nominal fluid and responsive to said second capacitance to provide a signal indication that the first and second plates are being subjected to said undesired fluid.

2. The invention of claim 1, wherein said signal indication means includes a capacitance to frequency convertor coupled to said capacitor.

3. The invention of claim 2, wherein said signal indication means further includes a frequency to voltage convertor coupled to said capacitance to frequency convertor.

4. The invention of claim 3, wherein said signal indication means further includes a Schmidt trigger coupled to said frequency to voltage convertor.

* * * * *